US010525134B2

(12) United States Patent
Yacoby-Zeevi et al.

(10) Patent No.: US 10,525,134 B2
(45) Date of Patent: *Jan. 7, 2020

(54) COMPOSITIONS COMPRISING APOMORPHINE AND ORGANIC ACIDS AND USES THEREOF

(71) Applicant: NeuroDerm, Ltd., Rehovot (IL)

(72) Inventors: Oron Yacoby-Zeevi, Moshav Bitsaron (IL); Mara Nemas, Rehovot (IL)

(73) Assignee: NeuroDerm, Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/809,137

(22) Filed: Nov. 10, 2017

(65) Prior Publication Data

US 2018/0303939 A1 Oct. 25, 2018

Related U.S. Application Data

(63) Continuation of application No. 14/405,913, filed as application No. PCT/IL2013/050487 on Jun. 5, 2013, now Pat. No. 9,999,674.

(60) Provisional application No. 61/655,633, filed on Jun. 5, 2012.

(51) Int. Cl.
| | | |
|---|---|---|
| A61K 31/167 | (2006.01) | |
| A61K 31/196 | (2006.01) | |
| A61K 31/245 | (2006.01) | |
| A61K 31/573 | (2006.01) | |
| A61K 47/18 | (2017.01) | |
| A61K 9/00 | (2006.01) | |
| A61K 31/473 | (2006.01) | |
| A61K 45/06 | (2006.01) | |
| A61K 31/485 | (2006.01) | |
| A61K 47/26 | (2006.01) | |
| A61K 47/22 | (2006.01) | |
| A61K 9/08 | (2006.01) | |
| A61K 9/10 | (2006.01) | |

(52) U.S. Cl.
CPC .......... *A61K 47/183* (2013.01); *A61K 9/0019* (2013.01); *A61K 9/08* (2013.01); *A61K 9/10* (2013.01); *A61K 31/473* (2013.01); *A61K 31/485* (2013.01); *A61K 45/06* (2013.01); *A61K 47/22* (2013.01); *A61K 47/26* (2013.01); *A61K 31/167* (2013.01); *A61K 31/196* (2013.01); *A61K 31/245* (2013.01); *A61K 31/573* (2013.01)

(58) Field of Classification Search
CPC .. A61K 31/167; A61K 31/196; A61K 31/245; A61K 31/44; A61K 31/473; A61K 31/573; A61K 47/00; A61K 9/08
See application file for complete search history.

(56) References Cited

U.S. PATENT DOCUMENTS

| | | |
|---|---|---|
| 3,936,495 A | 2/1976 | Sullivan, Jr. |
| 4,241,082 A | 12/1980 | Baba et al. |
| 4,409,233 A | 10/1983 | Tsukada et al. |
| 4,642,316 A | 2/1987 | Fawzi et al. |
| 4,684,666 A | 8/1987 | Haas |
| 4,816,568 A | 3/1989 | Hamilton, Jr. et al. |
| 4,826,875 A | 5/1989 | Chiesi |
| 4,963,568 A | 10/1990 | Schoenleber et al. |
| 5,284,512 A | 2/1994 | Koskan et al. |
| 5,350,769 A | 9/1994 | Kasai et al. |
| 5,861,423 A | 1/1999 | Caldwell et al. |
| 5,877,176 A | 3/1999 | Gross |
| 6,153,615 A | 11/2000 | Gross |
| 6,166,083 A | 12/2000 | Barrett et al. |
| 6,245,917 B1 | 6/2001 | Bosch et al. |
| 6,274,168 B1 | 8/2001 | Addicks et al. |
| 6,348,965 B1 | 2/2002 | Palladino et al. |
| 6,500,867 B1 | 12/2002 | Virkki et al. |
| 6,620,432 B2 | 9/2003 | Addicks et al. |
| 6,716,452 B1 | 4/2004 | Piccariello et al. |
| 6,878,529 B2 | 4/2005 | Harrow et al. |
| 6,974,591 B2 | 12/2005 | Kendrup et al. |
| 7,201,923 B1 | 4/2007 | van Lengerich |
| 7,223,776 B2 | 5/2007 | Surivet et al. |
| 7,309,719 B1 | 12/2007 | Aomatsu |
| 7,479,498 B2 | 1/2009 | Keller |
| 7,560,100 B2 | 7/2009 | Pinchasi et al. |
| 7,589,233 B2 | 9/2009 | Chandran |
| 7,709,494 B2 | 5/2010 | Defossa et al. |
| 7,863,336 B2 | 1/2011 | Yacoby-Zeevi et al. |
| 8,058,243 B2 | 11/2011 | Tyers et al. |
| 8,173,840 B2 | 5/2012 | Chandran |

(Continued)

FOREIGN PATENT DOCUMENTS

| | | |
|---|---|---|
| CN | 101669925 A | 3/2010 |
| DE | 2838232 A1 | 3/1979 |

(Continued)

OTHER PUBLICATIONS

"Duodopa Intestinal Gel," retrieved from https://www.medicines.org.uk/emc/medicine/20786/SPC/Duodopa+intestinal+gel/#composition, Sep. 5, 2014 (Sep. 5, 2015), pp. 1-7.
Anonymous, 'Consumer Medicine Information Madopar,' Roche Products (New Zealand) Limited (Publ), Aug. 5, 2015 (Aug. 5, 2015), pp. 1-9.
Anonymous, (2002), 'Levodpa: Management of Parkinson's Disease,' Mov Disord, 17(Suppl. 4):S23-S37.
Berge, et al. (1977) "Pharmaceutical Salts," Journal of Pharmaceutical Sciences, 66(1): 1-19.
Bond, Andrew D. "What is a Co-Crystal?," Crystengcomm, Royal Society of Chemistry, Cambridge, Great Britain, vol. 9, Jan. 1, 2007, pp. 833-834.

(Continued)

*Primary Examiner* — Zohreh A Fay
(74) *Attorney, Agent, or Firm* — Goodwin Procter LLP

(57) ABSTRACT

The present invention provides stable liquid or semi-solid pharmaceutical compositions of apomorphine, more particularly composition comprising apomorphine and an organic acid, which are useful in treatment of neurological or movement diseases or disorders, e.g., Parkinson's disease, or conditions associated therewith.

16 Claims, 3 Drawing Sheets

(56) References Cited

U.S. PATENT DOCUMENTS

| | | | |
|---|---|---|---|
| 8,193,243 | B2 | 6/2012 | Yacoby-Zeevi et al. |
| 8,263,125 | B2 | 9/2012 | Vaya et al. |
| 9,040,578 | B2 | 5/2015 | Yacoby-Zeevi et al. |
| 9,381,249 | B2 | 7/2016 | Yacoby-Zeevi et al. |
| 9,999,674 | B2 | 6/2018 | Yacoby-Zeevi et al. |
| 2002/0028799 | A1 | 3/2002 | Naylor et al. |
| 2002/0086876 | A1 | 7/2002 | Ruff et al. |
| 2002/0099013 | A1 | 7/2002 | Piccariello et al. |
| 2003/0119714 | A1 | 6/2003 | Naylor et al. |
| 2005/0053669 | A1 | 3/2005 | Friedl et al. |
| 2005/0090518 | A1 | 4/2005 | Quay |
| 2005/0163850 | A1 | 7/2005 | Wong et al. |
| 2005/0233945 | A1 | 10/2005 | Brown et al. |
| 2006/0004190 | A1 | 1/2006 | Holick et al. |
| 2006/0041014 | A1 | 2/2006 | Naylor et al. |
| 2006/0159751 | A1 | 7/2006 | Gogia et al. |
| 2006/0241183 | A1 | 10/2006 | Karoum |
| 2007/0003621 | A1 | 1/2007 | Nangia et al. |
| 2007/0148238 | A1 | 6/2007 | Nangia et al. |
| 2007/0269482 | A1 | 11/2007 | Sebree et al. |
| 2008/0051459 | A1 | 2/2008 | Nyholm et al. |
| 2008/0096847 | A1 | 4/2008 | Guertin |
| 2008/0248991 | A1 | 10/2008 | Dyer et al. |
| 2008/0255235 | A1 | 10/2008 | Segrell |
| 2008/0299204 | A1 | 12/2008 | Nangia et al. |
| 2010/0249170 | A1 | 9/2010 | Watts et al. |
| 2010/0298428 | A1 | 11/2010 | Yacoby-Zeevi et al. |
| 2011/0150946 | A1* | 6/2011 | Al-Ghananeem .... A61K 9/0021 424/400 |
| 2011/0190356 | A1 | 8/2011 | Bozik et al. |
| 2011/0250300 | A1 | 10/2011 | Biswal et al. |
| 2011/0269833 | A1 | 11/2011 | Yacoby-Zeevi et al. |
| 2012/0115823 | A1 | 5/2012 | Price et al. |
| 2013/0116215 | A1 | 5/2013 | Coma et al. |
| 2013/0123485 | A1 | 5/2013 | Park et al. |
| 2013/0253056 | A1 | 9/2013 | Nemas et al. |
| 2013/0338143 | A1 | 12/2013 | Yacoby-Zeevi et al. |
| 2014/0051755 | A1 | 2/2014 | Yacoby-Zeevi et al. |
| 2014/0249228 | A1 | 9/2014 | Yacoby-Zeevi et al. |
| 2014/0249229 | A1 | 9/2014 | Yacoby-Zeevi et al. |
| 2014/0249230 | A1 | 9/2014 | Yacoby-Zeevi et al. |
| 2014/0249231 | A1 | 9/2014 | Yacoby-Zeevi et al. |
| 2015/0182523 | A1 | 7/2015 | Yacoby-Zeevi et al. |
| 2016/0067339 | A1 | 3/2016 | Yacoby-Zeevi et al. |
| 2017/0368052 | A1 | 12/2017 | Yacoby-Zeevi et al. |
| 2018/0140610 | A1 | 5/2018 | Yacoby-Zeevi et al. |

FOREIGN PATENT DOCUMENTS

| | | | |
|---|---|---|---|
| EP | 1077692 | A1 | 2/2001 |
| EP | 1270007 | A2 | 1/2003 |
| EP | 2545905 | A1 | 1/2013 |
| GB | 2343376 | A | 5/2000 |
| IN | 244675 | B | 12/2010 |
| IN | 251149 | B | 2/2012 |
| JP | 54-50700 | A | 4/1979 |
| JP | 2000-204036 | A | 7/2000 |
| RU | 2370261 | C2 | 10/2009 |
| SU | 72463 | A2 | 11/1947 |
| SU | 555887 | A1 | 4/1977 |
| WO | WO-1993/12812 | | 7/1993 |
| WO | WO-1993/19773 | | 10/1993 |
| WO | WO-1998/31368 | A1 | 7/1998 |
| WO | WO-2000/054773 | A1 | 9/2000 |
| WO | WO-2001/001984 | A1 | 1/2001 |
| WO | WO-2005/099678 | A1 | 10/2005 |
| WO | WO-2006/006929 | A1 | 1/2006 |
| WO | WO-2006/120412 | A1 | 11/2006 |
| WO | WO-2007/138086 | A1 | 12/2007 |
| WO | WO-2008/133884 | A2 | 11/2008 |
| WO | WO-2010/134074 | A1 | 11/2010 |
| WO | WO-2012/006959 | A1 | 1/2012 |
| WO | WO-2012/010896 | A1 | 1/2012 |
| WO | WO-2012/066538 | A1 | 5/2012 |
| WO | WO-2013/007381 | A1 | 1/2013 |
| WO | WO-2013/183055 | A1 | 12/2013 |
| WO | WO-2016/042413 | A1 | 3/2016 |
| WO | WO-2016/103262 | A2 | 6/2016 |

OTHER PUBLICATIONS

Chun IK et al., (2011), 'Design and Evaluation of Levodopa Methyl Ester Intranasal Delivery Systems,' J Parkinson's Dis, 1(1):101-7.
Gordon M et al., (2006), 'Intravenous Levodopa Administration in Humans Based on a Two-Compartment Kinetic Model,' J Neurosci Methods, 159(2):300-7.
Hirano A et al., (2008), 'Arginine Increases the Solubility of Coumarin: Comparison with Salting-in and Salting-out Additives,' J Biochem, 144(3):363-9.
International Preliminary Report on Patentability and Written Opinion of the International Searching Authority for PCT/IL2013/050487, dated Dec. 9, 2014 (7 pages).
International Search Report for International Application No. PCT/IL2010/000400, dated Jul. 29, 2010 (4 pages).
International Search Report for International Application No. PCT/IL2011/000881, dated Apr. 3, 2012 (4 pages).
International Search Report for International Application No. PCT/IL2014/050261, dated May 30, 2014 (5 pages).
International Search Report for International Application PCT/IL2015/051246, dated Jul. 6, 2016 (6 pages).
International Search Report for PCT/IB2015/002139, dated Feb. 26, 2016, 3 pages.
International Search Report for PCT/IL2013/050487, dated Sep. 19, 2013 (3 pages).
International Search Report for PCT/IL2015/050258 dated Aug. 13, 2015 (3 pages).
International Searching Authority, International Preliminary Report on Patentability (Form IB/373) and Written Opinion (Form ISA/237) for International Application No. PCT/IB2015/002139, dated Mar. 21, 2017, 7 pages.
International Searching Authority, International Preliminary Report on Patentability (Form IB/373) and Written Opinion (Form ISA/237) for International Application No. PCT/IL2015/051246, dated Jun. 27, 2017, 11 pages.
Martinez M et al., (1999), 'Hypothesis: Can N-Acetylcysteine Be Beneficial in Parkinson's Disease?,' Life Sci, 64(15):1253-7.
Mehlisch DR et al., (2002), 'A Controlled Comparative Study of Ibuprofen Arginate Versus Conventional Ibuprofen in the Treatment of Postoperative Dental Pain,' J Clin Pharmacol, 42(8):904-11.
Meshul CK et al., (2002), 'Nicotine Alters Striatal Glutamate Function and Decreases the Apomorphine-Induced Contralateral Rotations in 6-OHDA-Lesioned Rats,' Exp Neurol, 175(1):257-74.
Morrison, et al. (1974) Organic Chemistry, 6th Ed., (Abstract only) (1 page).
Nahata MC et al., (2000), 'Development of Two Stable Oral Suspensions of Levodopa-Carbidopa for Children with Amblyopia,' J Pediatr Ophthalmol Strabismus, 37(6):333-7.
Nord M, (2010), 'The Effect of Peripheral Enzyme Inhibitors on Levodopa Concentrations in Blood and CSF,' Mov Disord, 25(3):363-7.
Nutt JG et al., (1997), 'Motor Fluctuations During Continuous Levodopa Infusions in Patients with Parkinson's Disease,' 12(3):285-92.
Nyholm D, (2006), 'Enteral Levodopa/Carbidopa Gel Infusion for the Treatment of Motor Fluctuations and Dyskinesias in Advanced Parkinson's Disease,' Expert Rev Neurother, 6(10):1403-11.
Nyholm D, (2010), Pharmacokinetics of Levodopa/Carbidopa Infusion With and Without Oral Catechol-O-methyl Transferase (COMT) Inhibitors (DuoCOMT), ClinicalTrials.gov Identifier: #NCT00906828.
Nyholm D, (2012), 'Levodopa Infusion Combined with Entacapone or Tolcapone in Parkinson Disease: A Pilot Trial,' Eur J Neurol,19(6):820-6.
Olanow CW, (2008), 'Levopoda/Dopamine Replacement Strategies in Parkinson's Disease—Future Directions,' Mov Disord, 23(Suppl 3):S613-S622.

(56) References Cited

OTHER PUBLICATIONS

Pappert EJ et al., (1997) 'Clinical/Scientific Notes—The Stability of Carbidopa in Solution,' Mov Disord, 12(4):608-10.
Pardo B et al., (1993), 'Ascorbic Acid Protects Against Levodopa-Induced Neurotoxicity on a Catecholamine-Rich Human Neuroblastoma Cell Line,' Mov Disord, 8(3):278-84.
Pschorr et al. "Uber Die Constitution des Apomorphins", Berichte der Deutschen Chemischen Gesellschaft, vol. 35, No. 4, Oct. 17, 1902, pp. 4377-4392.
Redenti E, (2001), 'Cyclodextrin Complexes of Salts of Acidic Drugs. Thermodynamic Properties, Structural Features, and Pharmaceutical Applications,' J Pharm Sci, 9(8): 979-86.
Russian Office Action for Application No. 2014152208/15 dated Aug. 31, 2017, and its English translation (11 pages).
Russian Office Action for Application No. 2014152208/15 dated Nov. 14, 2017, and its English translation (16 pages).
Steiger MJ et al., (1991), 'The Clinical Efficacy of Oral Levodopa, Methyl Ester Solution in Reversing Afternoon "off" Periods in Parkinson's Disease,' Clin Neuropharmacol, 14(3):241-4.
Tiffeneau: Bulletin de la Societe Chimique de France, Societe Francaise de Chime. Paris, France, vol. 4, Jan. 1, 1915, pp. 109-119.
Touchon JC et al., (2005), 'Apomorphine-induced Alterations in Striatal and *Substantia Nigra Pars* Reticulata Glutamate Following Unilateral Loss of Striatal Dopamine,' Exp Neurol, 193(1):131-40.
Tsai M-J, (2010), 'Oral Apomorphine Delivery from Solid Lipid Nanoparticles with Different Monostearate Emulsifiers: Pharmacokinetic and Behavioral Evaluations,' J Pharm Sci, 100(2):547-57.
Tsumoto K et al., (2004), 'Role of Arginine in Protein Refolding, Solubilization, and Purification,' Biotechnol Prog, 20(5):1301-8.
Written Opinion of the International Searching Authority for International Application No. PCT/IL2010/000400 dated Aug. 29, 2010 (8 pages).
Written Opinion of the International Searching Authority for International Application No. PCT/IL2011/000881, dated Apr. 3, 2012 (7 pages).
Written Opinion of the International Searching Authority for International Application No. PCT/IL2014/050261, dated May 30, 2014 (6 pages).
Written Opinion of the International Searching Authority for PCT/IL2015/050258, dated Aug. 13, 2015 (6 pages).
Yacoby-Zeevi O et al., (2010), 'Markedly Enhanced Levodopa Pharmacokinetics from Continuous Subcutaneous Carbidopa Administration,' Eur J Neurol, 17(Suppl s3):52.
Hirano, A, et al. (2010) 'Arginine-assisted solubilization system for drug substances: solubility experiment and simulation,' *J Phys Chem B*, 114(42):13455-62. (Abstract only.).
Morissette, SL, et al. ( 2003) 'High-throughput Crystallization: Polymorphs, Salts, Co-Crystals and Solvates of Pharmaceutical Solids,' *Advanced Drug Delivery Reviews*, 56: 275-300.
Russian Office Action for Application No. 2017123762/04 dated Jun. 11, 2019 (English translation) (6 pages).

* cited by examiner

COMPOSITIONS COMPRISING APOMORPHINE AND ORGANIC ACIDS AND USES THEREOF

CROSS REFERENCE TO RELATED APPLICATIONS

This application is a continuation of U.S. patent application Ser. No. 14/405,913, filed Dec. 5, 2014, which is the U.S. national stage of International (PCT) Patent Application No. PCT/IL2013/050487, filed Jun. 5, 2013, which claims the benefit of U.S. Provisional Patent Application No. 61/655,633 filed Jun. 5, 2012, the entire contents of each of which are herein incorporated by reference for all purposes.

TECHNICAL FIELD

The present invention is generally directed to stable liquid or semi-solid pharmaceutical compositions of apomorphine, and uses thereof in treating neurological diseases or disorders, including Parkinson's disease, or conditions associated therewith.

BACKGROUND ART

Parkinson's disease is a progressive degenerative disease of the central nervous system. Although the primary cause of Parkinson's disease is not known, it is characterized by the degeneration of dopaminergic neurons of the substantia nigra. The substantia nigra is located in the midbrain and is involved in controlling voluntary movements. The degeneration of neurons causes a shortage of dopamine in the brain, which is believed to cause the observable symptoms of the disease. These symptoms include paucity of movement and rigidity, resting tremor, bradykinesia, and poor balance.

There are a variety of therapeutic treatments available for Parkinson's disease. The best known is levodopa, a dopamine precursor; however, treatment with levodopa can cause serious side-effects, especially over a long term. One such complication of long-term treatment with levodopa is the development of rapid fluctuations in clinical state, where a patient switches suddenly between mobility and immobility for periods ranging from a few minutes to a few hours. This phenomenon is known as the "on-off effect", the "on" state characterized by the levodopa benefit of early normal motor functioning and the "off" state characterized by akinesia—abrupt loss of mobility e.g, where a patient may suddenly stop while walking. Approximately half of patients on levodopa therapy will develop such on-off effects after several years or therapy.

While apomorphine hydrochloride has proved effective in treating "off" episodes patients with Parkinson's disease, a common and serious side effect of administering apomorphine hydrochloride by subcutaneous injection is the development of subcutaneous nodules at the injection site, which can become infected, necessitating treatment or surgical involvement. A majority of people on infused apomorphine develop nodules, and a new nodule may form every time the infusion needle is re-sited, which may happen on a daily basis. Such nodules may be painful, limit available infusion sites and interfere with absorption. Further, unstable compositions, e.g., having precipitate of apomorphine or other agents, may be the cause, or exacerbate, such nodule side effects. Thus, there is a need for new, stable formulations of apomorphine which are safe and effective for administration to patients.

SUMMARY OF INVENTION

This disclosure relates at least in part to the discovery that certain organic acids, e.g., acidic amino acids, form stable salts of apomorphine that are suitable for compositions allowing for subcutaneous administration without unwanted side effects.

In one aspect, the present invention thus relates to a stable liquid or semi-solid pharmaceutical composition, particularly an aqueous pharmaceutical composition, comprising apomorphine, an organic acid, e.g., an acidic amino acid, and a pharmaceutically acceptable carrier, wherein the molar ratio of apomorphine to the organic acid is about 1 to about 0.5-2.5, or about to about 0.5-1.5, e.g., 1:1.2.

In another aspect, the present invention relates to a liquid or semi-solid pharmaceutical composition comprising (i) apomorphine or a salt thereof; and (ii) either an emulsifier or surfactant, or both emulsifier and surfactant, wherein the composition has substantially no precipitation of solids, for at least 48 hours at 25° C. within a pH ranging from about 3 to about 7.5, or at a pH greater than 4.

In a further aspect, the present invention provides a method of treating a neurological or movement disease or disorder, or a condition associated therewith, in a patient in need thereof, by administering a pharmaceutical composition as disclosed herein. In one embodiment, the method of the invention is aimed at treating a neurological disease or disorder characterized by reduced levels of dopamine in a patient's brain, Parkinson's disease, by administering the disclosed composition.

In one particular such aspect, the present invention thus provides a method of treating Parkinson's disease in a patient in need thereof by administering a composition as disclosed herein.

In another particular such aspect, the present invention provides a method of treating akinesia in a patient in need thereof, comprising administering to the patient a composition as disclosed herein, wherein the patient has been treated with levodopa.

In still another aspect, the present invention relates to a liquid or semi-solid pharmaceutical composition as defined above, for treatment of a neurological or movement disease or disorder, or a condition associated therewith.

In yet another aspect, the present invention relates to a liquid or semi-solid pharmaceutical composition as defined above, for use in treatment of a neurological or movement disease or disorder, or a condition associated therewith.

DETAILED DESCRIPTION OF THE INVENTION

Compositions

Figure 1:
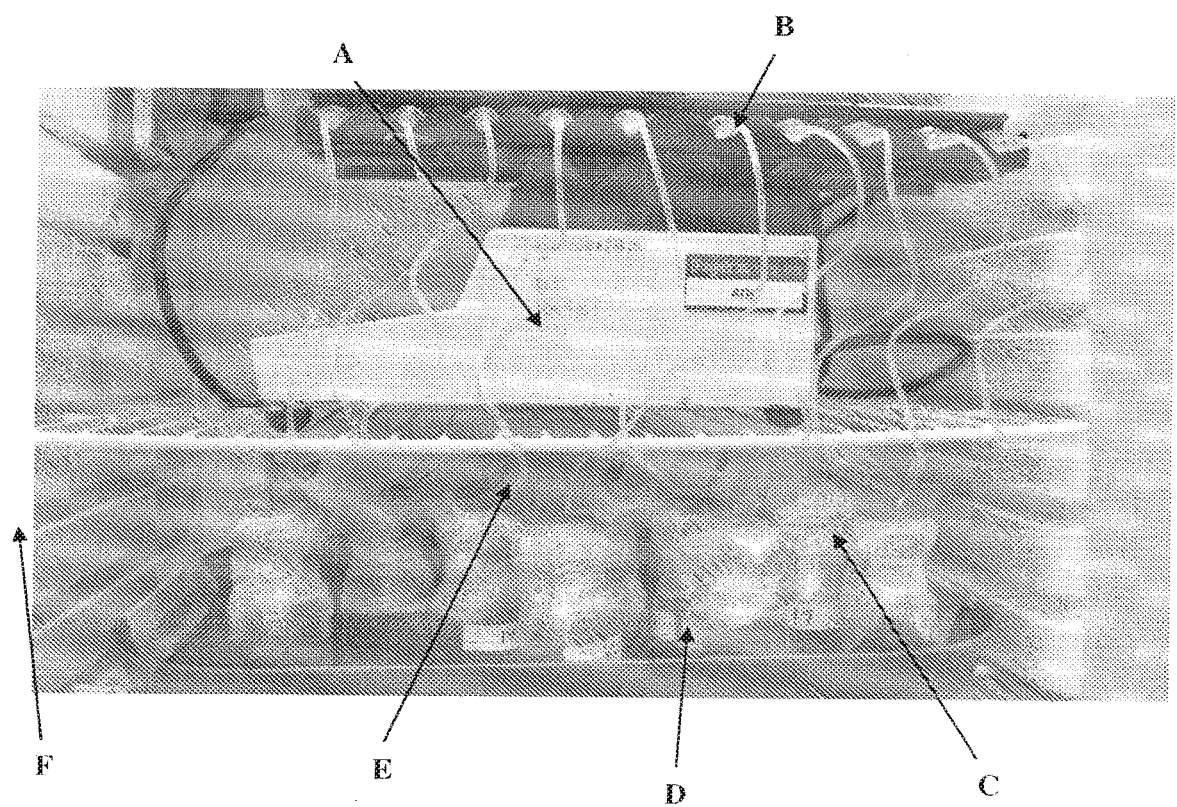
FIG. 1 shows the system used for evaluating the effect of apomorphine formulation composition on pig skin staining. Infusion pump set at 0.05 ml/h (A); Formulation delivered using a 22 G butterfly (B); Full thickness pig skin (cutis and subcutis) is placed on top of a bottle containing PBS. The skin is directly in contact with the PBS. The skin and bottle are covered with parafilm to protect the system front air as much as possible (C); A 100 ml bottle filled to the top with warm PBS (D); Formulation, 0.4 ml, was administered subcutaneously via a 22 G needle, at 0.05 ml/h (total of 8 h) (E): and Incubator set at 37° C. Samples were incubated for a period of about 17 h (F).

In one aspect, the present invention relates to a stable liquid or semi-solid Pharmaceutical composition, particularly an aqueous pharmaceutical composition, comprising apomorphine and an organic acid. Exemplary organic acids include, without being limited to, amino acids, carboxylic acids, and, dicarboxylic acids. For example, contemplated carboxylic acids and/or dicarboxylic acids for use in the claimed composition may contain at least two, three, or four carbon atoms, e.g., tartaric acid. Contemplated dicarboxylic acids for use in the claimed compositions may be hydrophilic or substituted with hydrophilic groups, e.g., hydroxyl groups.

In certain embodiments, the contemplated compositions may include apomorphine and an amino acid, e.g., a natural or unnatural amino acid. Contemplated amino acids for use in the claimed compositions may be, without limiting, acidic natural amino acids such as aspartic acid or glutamic acid, or acidic unnatural amino acids such as cysteic acid.

Contemplated herein, e.g., is a stable pharmaceutical composition comprising apomorphine and an organic acid, where the molar ratio of apomorphine to the organic acid is about 1 to about 0.5, or about 1.0 to about 2.5, or about 1 to about 0.5 to 1.5 (e.g., about 1:0.5 to about 1.0 to about 1.5). For example, in certain embodiments, the molar ratio of apomorphine to the organic acid is about 1:0.5, or about 1:0.6, or about 1:0.7, or about 1:0.8, or about 1:0.9, or about 1:1, or about 1:1.1, or about 1:1.2, or about 1:1.3, or about 1:1.4, or about 1:1.5, or about 1:1,6, or about 1:1.7, or about 1:1.8, or about 1:1.9, or about 1:2.0, or about 1:2.1, or about 1:2.2, or about 1:2.3, or about 1:2.4, or about 1:2.5.

In a particular embodiment, contemplated herein is a stable pharmaceutical composition comprising, apomorphine and an, amino acid, where the molar ratio of apomorphine to the amino acid is about 1 to about 0.5-2.5. For example, in certain embodiments, the molar ratio of apomorphine to the amino acid is about 1:0.5, or about 1:0.6, or about 1:0.7, or about 1:0.8, or about 1:0.9, or about 1:1, or about 1:1.1, or about. 1:1.2, or about 1:1.3, or about 1:1.4, or about 1:1.5, or about 1:1.6, or about 1:1.7, or about 1:1,8, or about 1:1.9, or about 1:2.0, or about 1:2.1, or about 1:2.2, or about 1:2,3, or about 1:2.4, or about 1:2.5. In more particular embodiments, the amino acid is an acidic amino acid such as, without being limited to, aspartic acid, glutamic acid, or a combination thereof.

In certain embodiments, the pharmaceutical composition has a pH of about or greater than 3 at 25° C. In certain particular embodiments, the pharmaceutical composition has a pH between about 3.0 and about 5.5, more particularly between about 3.0 and about 5.0 at 25° C. In more particular embodiments, the composition has a pH between about 3.1 and about 4.9, about 3.2 and about 4.8, about 3.3 and about 4.7, about 3.4 and about 4.6, about 3.5 and about 4.5, about 3.6 and about 4.4, about 3.7 and about 4.3, about 3.8 and about 4.2, or about 3.9 and about 4.1 at 25° C. In other embodiments, the pH of the composition is about 4 at 25° C. In other particular embodiments, the pharmaceutical composition has a pH between about 4.0 and about 5.0, or between about 4.0 and about 7.5, at 25° C.

In certain embodiments, the pharmaceutical composition comprises at least about 1% by weight apomorphine. In some embodiments, the composition comprises about 1% to about 4% by weight apomorphine, e.g., about 1.25%, about 1.5%, about 1.75%, about 2%, about 7.25%, about 2.5%, about 2.75%, about 3%, about 3.25%, about 3.5%, about 3.75%, or about 4% by weight apomorphine. In other embodiments, a contemplated composition comprises about 1% to about 2.5% by weight apomorphine, or about 0.5% to about 3% by weight apomorphine, or about 1.1% to about 2.6% by weight or more apomorphine.

In certain embodiments, the pharmaceutical compositions of the present invention are stable for 24 hours, or for at least 24 hours, or more, at room temperature, e.g., at 20° C. to 30° C., e.g., at 25° C. For example, in some embodiments, the disclosed compositions are stable for 24 hours, for at least 48 hours, or for 7 days or more, at 25° C. In particular embodiments the disclosed pharmaceutical compositions are stable for at least 48 hours at 25° C., or are even stable for longer periods at room temperature, e.g., for 3 days, 1 week, month, or longer.

In certain embodiments, the pharmaceutical composition has substantially no precipitation of solids for at least 24 hours, 48 hours, 7 days, or 2 months, e.g., at 20° C. to 30° C., e.g., at 25° C. In a particular embodiment, the pharmaceutical composition has substantially no precipitation of solids for at least 48 hours at, e.g., 20° C. to 30° C., e.g., at 25° C.

In certain embodiments, the pharmaceutical composition of the present invention further comprises an amino sugar, a basic amino acid, one or more antioxidants, or a combination thereof.

In certain particular embodiments, the pharmaceutical compositions of the invention further comprises an amino sugar such as, without being limited to, meglumine, and may also comprise a basic amino acid and one or more antioxidants. Particular such compositions comprise apomorphine, aspartic acid and/or glutamic acid, and meglumine.

In certain particular embodiments, the pharmaceutical compositions of the invention further comprises a basic amino acid such as, without limiting, arginine, and may also comprise an amino sugar and one or more antioxidants. Particular such compositions comprise apomorphine, aspartic acid and/or glutamic acid, and arginine.

In certain particular embodiments, the pharmaceutical compositions of the present invention further comprises at least one, i.e., one, two, three or more, antioxidant, an agent that inhibits the formation of oxidation products. Such an agent may be, e.g., tyrosinase inhibitors and/or o-quinone scavengers and/or $Cu^{++}$ chelators and/or antioxidants, and/or tetrahydroquinolines. For example, contemplated formulations may include o-quinone scavengers such as, but not limited to, N-acetyl cysteine, glutathione, ascorbic acid, Na-ascorbate, and/or L-cysteine. For example, a contemplated formulation may include ascorbic acid and a cysteine, L-cysteine or N-acetyl cysteine. In a contemplated formulation, the ratio of ascorbic acid to another antioxidant, e.g., L-cysteine or N-acetyl cysteine, may exist at a particular weight-to-weight ratio such as about 1:1, about 2:1, about 3:1, about 4:1, about 5:1, about 6:1, about 7:1, about 8:1, about 9:1, or about 10:1. In some embodiments, formulations may include an agent chosen from one or more of tyrosinase inhibitors such as captopril, methimazole, quercetin, arbutin, aloesin, N-acetylglucoseamine, retinoic acid, β-tocopheryl ferulate, MAP (Mg ascorbyl phosphate), substrate analogues (e.g., sodium benzoate, L-phenylalanine), $Cu^{++}$ chelators (for example, $Na_2$-EDTA, $Na_2$-EDTA-Ca), DMSA (succimer), DPA (D-penicillamine), trientine-HCl, dimercaprol, clioquinol, sodium thiosulfate, TETA, TEPA, curcumin, neocuproine, tannin, and/or cuprizone. Other contemplated anti-oxidants that may form part of a disclosed formulation include sulfite salts, e.g., sodium hydrogen sulfite or sodium metabisulfite, di-tert-butyl methyl phenols, tert-butyl-methoxyphenols, polyphenols, tocopherols and/or ubiquinones, including but not limited to caffeic acid.

Contemplated antioxidants that can be included in disclosed compositions may be selected from, e.g., thiols such as aurothioglucose, dihydrolipoic acid, propylthiouracil, thioredoxin, glutathione, cysteine, cystine, cystamine, and thiodipropionic acid; sulphoxitnines such as buthionine-sulphoximines, homo-cysteine-sulphoximine, buthionine-sulphones, and penta-, hexa- and heptathionine-sulphoximine; metal chelators such as α-hydroxy-fatty acids, palmitic acid, phytic acid, lactoferrin, citric acid, lactic acid, malic acid, humic acid, bile acid, bile extracts, bilirubin, biliverdin, EDTA, EGTA, and DTPA; sodium metabisulfite; vitamins such as vitamin E, vitamin C, ascorbyl palmitate, Mg ascorbyl phosphate, and ascorbyl acetate; phenols such as butythydroxytoluene, butylhydroxyanisole, ubiquinol, nordihydroguaiaretic acid, and trihydroxybutyrophenone; benzoates such as coniferyl benzoate; uric acid; mannose; propyl gallate; selenium such as selenium-methionine; stilbenes such as stilbene oxide and trans-stilbene oxide; and combinations thereof.

In particular embodiments, a contemplated pharmaceutical composition further comprises one or more antioxidants each independently selected from ascorbic acid, Na-ascorbate, L-cysteine, N-acetylcysteine (NAC), glutathione (GSH), $Na_2$-EDTA, $Na_2$-EDTA-Ca, or sodium bisulfite. In specific such embodiments, a contemplated pharmaceutical composition further comprises ascorbic acid and/or sodium bisulfite.

In certain embodiments, the pharmaceutical composition of the present invention further comprises a surfactant, i.e., a compound that lowers the surface tension of a liquid. Non-limiting examples of suitable surfactants include polysorbate surfactants such as Tween-80, Tween-60, Tween-40, Tween-20, Tween-65 and Tween-85, and sorbitans surfactants such as Span 20, Span 40, Span 60, Span 80 and Span 85. In a particular such embodiment, the pharmaceutical composition of the invention further comprises Tween-80.

In certain embodiments, the pharmaceutical composition of the present invention further comprises a local anesthetic, i.e., a drug, which causes a reversible loss of sensation for a limited region of the body while maintaining consciousness, and/or an anti-inflammatory agent, Examples of local anesthetics include, without being limited to, amide based local anesthetics such as lidocaine, prilocaine, bupivicaine, levobupivacaine, ropivacaine, mepivacaine, dibucaine, and etidocine, and ester based local anesthetics such as procaine, amethocaine, cocaine, benzocaine, and tetracaine. Examples of anti-inflammatory agents include; without limiting, non-steroidal anti-inflammatory agents such as diclofenac, ketorolac, salicylates ibuprofen, piroxicam, and benzy-damine, and steroidal anti-inflammatory agents such as prednisone, dexmethasone, betamethasone, prednisone hydrocortisone or salts thereof.

The pharmaceutical composition of the present invention may be liquid solutions, i.e., substantially homogeneous liquid mixtures at room temperature, e.g., at 25° C., or semi-solid solutions formulated, e.g., as a gel, gum, or candy. Such liquid or semi-solid mixtures may comprise water and/or other pharmaceutically acceptable carriers or excipients. In a particular embodiment, the disclosed composition is substantially aqueous.

In certain embodiments, a disclosed liquid or semi-solid formulation will be stable for a period of 1 day, 2 days, 3 days, 1 week, 1 month, or more at room temperature. In certain embodiments, the pharmaceutical composition as defined herein further comprises a pharmaceutically acceptable excipient such as, without being limited to, Tween-80, Tween-60, Tween-40, Tween-20, N-methylpyrrolidone (NMP), or polyvinylpyrrolidone (PVP), EDTA (or salts thereof), cysteine, N-acetylcysteine, and/or sodium bisulfite.

In certain embodiments, the compositions are stable lyophilized powders. The lyophilized powders can be reconstituted into a liquid formulation by addition of water alone or water and a pharmaceutically acceptable carrier, and may or may not include anti-oxidants.

In another aspect, the present invention relates to a stable liquid or semi-solid pharmaceutical composition, particularly an aqueous pharmaceutical composition, comprising (1) apomorphine or a salt thereof; and (ii) either an emulsifier or surfactant, or both emulsifier and surfactant. In one particular such aspect, the composition comprises apomorphine, and an emulsifier, surfactant, or both. In another particular such aspect, the composition comprises a salt of apomorphine, and an emulsifier, surfactant, or both. The apomorphine salt may be any salt formed by reacting apomorphine with an organic acid. Particular organic acids include, without limiting, amino acids, more particularly acidic amino acid such as aspartic acid, glutamic acid and cysteic acid, as well as carboxylic acids and dicarboxylic acids containing at least two, three, or four carbon atoms, e.g., tartaric acid. Particular such compositions have substantially no precipitation of solids, for at least 4 hours at 25° C. within a pH ranging from about 3 to about 7.5, or at a pH greater than 4. These compositions may be liquid solutions, substantially homogeneous liquid mixtures at room temperature, at 25° C., or semi-solid solutions formulated, e.g., as a gel, gum, or candy, and may comprise water and/or other pharmaceutically acceptable carriers or excipients. In particular embodiments, the disclosed compositions are substantially aqueous.

In certain embodiments, the pharmaceutical composition comprises at least 1% by weight apomorphine, or about 1% to about 4%, e.g., about 1.25%, about 1.5%, about 1.75%, about 2%, about 2.25%, about 2.5%, about 2.75%, about 3%, about 3.25%, about 3.5%, about 3.75%, or about 4%, by weight apomorphine.

In certain embodiments, the pharmaceutical composition disclosed comprises 0.01% to 4%, e.g., 0.01%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.2%, 2.4%, 2.6%, 2.8%, 3.0%, 3.2%, 3.4%, 3.6%, 3.8%, or 4.0%, emulsifier or surfactant.

In certain embodiments, the pharmaceutical composition defined hereinabove may further comprise one or more, i.e., one, two, three or more, antioxidants, as defined above. In particular embodiments, a contemplated pharmaceutical composition further comprises one or more antioxidants each independently selected from ascorbic acid, Na-ascorbate. L-cysteine, NAC, GSH, $Na_2$-EDTA, $Na_2$-EDTA-Ca, or sodium bisulfite.

In certain embodiments, a stable pharmaceutical composition of the present invention may be suitable for subcutaneous, intravenous, intranasal, transdermal, sublingual, intramuscular, buccal, ocular, or intratracheal administration. In some embodiments, the composition is continuously infused, e.g, subcutaneously via a small pump. In some embodiments, the composition is inhaled. In some embodiments, the composition is administered parenterally.

The disclosed compositions may be administered subcutaneously and/or, substantially continuously. When administered subcutaneously and/or dermally, such compositions having apomorphine or a pharmaceutically acceptable salt thereof, and an organic acid, e.g., an acidic amino acid, may result in minimal local tissue damage, e.g., as compared to subcutaneous or dermal administration of a composition that includes apomorphine-HCl. Further, such apomorphine/organic acid compositions, when further including a basic amino acid such as arginine, and/or a basic amino sugar such as meglumine, and/or a surfactant such as Tween-80, may have more stability, e.g., may not precipitate and/or Form unwanted oxidation products over time as compared to a composition having apomorphine-HCl. Further, such apomorphine/organic acid compositions, when further including, a surfactant such as Tween-80 may have more stability, e.g., may not precipitate and/or form unwanted oxidation products over time as compared to a composition having apomorphine without a surfactant. As contemplated herein, subcutaneous administration may comprise the use of one or more infusion pumps and/or transdermal and/or dermal patches. Alternatively, a disclosed composition may be administered intraduodenally, intranasally, sublingually, intramuscularly, ocularly, buccally, intratracheally or intravenously.

As used herein in the specification, the term "organic acid" refers to an organic compound with acidic properties such as carboxylic acids, dicarboxylic acids, sulfonic acids, alcohols, hydroxy acids, thiols, and thio-acids. For example, the organic acids for use in the claimed composition may contain at least two, three or four carbon atoms, e.g., tartaric acid. Examples of organic acids include, but are not limited to, amino acids such as aspartic acid, glutamic acid, and arginine, and dicarboxylic acids such as fumaric acid, oxalic acid, malonic acid, succinic acid, glutaric acid, maleic acid, and the like. Further examples of organic acids include lactic acid, malic acid, aconitic acid, citric acid, alycolic acid, ascorbic acid, formic acid, acetic acid, tartaric acid, and glucuronic acid.

The term "natural amino acid" refers to any of the amino acids found in proteins. Examples of natural amino acids include, but are not limited to, alanine, arginine, aspartic acid, glutamic acid, histidine, lysine, and the like.

The term "non-natural amino acid" refers to non-proteinogenic amino acids that either occur naturally or are chemically synthesized. Examples of non-natural amino acids include, but are not limited to, ornithine, β-alanine, 2-aminoadipic acid, 3-aminoadipic acid, γ-carboxyglutamic acid, hydroxylysine, 4-guanidinobutyric acid, 3-guanidinopropionic acid, 4-azidobutanoic acid, 5-azidopentanoic acid, and the like. Both D- and L-amino acids are contemplated herein.

The term "amino sugar" refers to a monosaccharide in which a non-glycosidic hydroxyl group is replaced by an amino or substituted amino group, such as meglumine, D-glucosamine, sialic acid. N-acetylglucosamine, galactosamine, and the like.

The term "anti-oxidant" refers to an agent that inhibits the formation of oxidation products.

The term "emulsifier", also known as "emulgent", refers to a substance that stabilizes an emulsion by increasing its kinetic stability, e.g., a "surface active substance" or a surfactant. The term "surfactant" refers to a surface active substance, a compound that lowers the surface tension of a liquid, the interfacial tension between two liquids, or that between a liquid and a solid.

The term "pharmaceutical composition" as used herein refers to a composition comprising at least one active agent as disclosed herein, formulated together with one Or more pharmaceutically acceptable carriers.

The term "pharmaceutically acceptable carrier" or "pharmaceutically acceptable excipient" as used herein refers to any and all solvents, dispersion media, preservatives, anti-oxidants, coatings, isotonic and absorption delaying agents, surfactants, and the like, that are compatible with pharmaceutical administration. The use of such media and agents for pharmaceutically active substances is well known in the art. The compositions may contain other active compounds providing supplemental, additional, or enhanced therapeutic functions.

The terms "pharmaceutically acceptable" and "pharmacologically acceptable" include molecular entities and compositions that do not produce an adverse, allergic, or other untoward reactions when administered to an animal, or human, as appropriate. For human administration, preparations should meet sterility, pyrogenicity, general safety, and purity standards as required by a government drug regulatory agency, e.g., the United States Food and Drug Administration (FDA) Office of Biologics standards.

The term "physiologically acceptable pH" is understood to mean a pH of a composition that facilitates administration of the composition to the patient without significant adverse effects, e.g. a pH of about 3 to about 9.8 at 25° C., e.g., a pH of about 3.5±0.5 to about 9.5±0.3, or about 3.5 to about 9.5.

Methods

In a further aspect, the present invention provides a method, of treating a neurological or movement disease or disorder, or a condition associated therewith, in a patient in need thereof, comprising administering to said patient a pharmaceutical composition as disclosed herein.

The neurological or movement diseases or disorders treated by the method of the present invention are characterized by reduced levels of dopamine in the brain, and include restless leg syndrome, Parkinson's disease, secondary parkinsonism, Alzheimer's disease, Huntington's disease, Shy-Drager syndrome, dystonia. akinesia, alcohol and morphine addiction. erectile dysfunction, and conditions resulting from brain injury, including carbon monoxide or manganese intoxication.

In one particular embodiment, the invention provides a method of treating Parkinson's disease in a patient in need thereof, comprising administering to the patient a pharmaceutical composition as disclosed herein.

In another particular embodiment, the invention provides a method of treating akinesia in a patient in need thereof, comprising administering to the patient a pharmaceutical composition as disclosed herein, wherein the patient has been treated with levodopa.

In a further embodiment, the invention provides a method of treating a condition associated with a neurological disease or disorder in a patient in need thereof, comprising administering to the patient a pharmaceutical composition as disclosed herein. The neurological disease or disorder contemplated herein is Parkinson's disease, Alzheimer's disease, or akinesia, and the conditions associated with a neurological disease or disorder include, without limiting, alcoholism, opiate addiction, and erectile dysfunction.

In still another aspect, the present invention relates to a liquid pharmaceutical composition as defined above for treatment of a neurological or movement disease or disorder as defined herein, or a condition associated therewith.

In yet another aspect, the present invention relates to a liquid pharmaceutical composition as defined above, for use in treatment of a neurological or movement disease or disorder as defined herein, or a condition associated therewith.

As used herein in the specification, the term "neurological disease or disorder" refers to a disease or disorder of the body's nervous system.

The term "movement disorder" refers to a nervous system condition that causes abnormal voluntary or involuntary movements, or slow, reduced movements.

The term "treated with levodopa" includes past or present treatment of a patient with levodopa.

Kits

A contemplated kit may include an apomorphine salt or a liquid composition having apomorphine and an organic acid (and optionally an additional therapeutic agent, e.g., levodopa, carbidopa, or entacapone). Such a composition may be liquid or a lyophilized powder that can be reconstituted into a liquid formulation, or, for example, may form part of a transdermal patch, and may be designed for administration by any suitable route such as, but not limited to, transdermally, intravenously, subcutaneously, intradermally, intramuscularly, or intraduodenally.

In some embodiments, disclosed liquid compositions, e.g., comprising apomorphine and an organic acid, may be provided in, e.g., one, two or more pre-fined cartridges suitable for use by a patient or physician. For example, provided herein is a kit comprising a prefilled cartridge wherein a disclosed liquid formulation is disposed within the cartridge (e.g., a pre-filled cartridge having a single dose or a dose suitable for a single administration to a patient of an apomorphine and organic acid formulation (and optionally an additional therapeutic agent, e.g., levodopa or carbidopa)), and optionally instructions for use.

The invention now being generally described, it will be more readily understood by reference to the following examples which are included merely for purposes of illustration of certain aspects and embodiments of the present invention, and are not intended to limit the invention in any way.

EXAMPLES

Example 1. Preparation of Apomorphine Salt Solution/Formulation for Subcutaneous Administration Sodium bicarbonate 0.1 N solution was added to a 1% apomorphine-HCl solution. The apomorphine-HCl solution was derived from APO-GO®, a commercially available product comprising a 10 mg/ml apomorphine-HCl solution. The precipitate, being the apomorphine base, was washed twice with water. The precipitated apomorphine base was dissolved with either a 0.59% glutamic acid solution, 0.53% aspartic acid solution, or 0.6% tartaric acid solution, to form a final 1% apomorphine solution at a 1:1 molar ratio with the glutamic, aspartic, or tartaric acid, or a 1:0.5 molar ratio with the tartaric acid. In some instances, ascorbic acid and/or meglumine solutions were added to the apomorphine salt solutions to obtain a final concentration of 0.5% or 0.6%, respectively. Table 1 shows the composition of apomorphine formulations which were prepared as described above.

TABLE 1

Composition of apomorphine formulations

| | | | | | | | | | | |
|---|---|---|---|---|---|---|---|---|---|---|
| APO-GO ® (10 mg/ml) Apo•HCl) μl | 1000 | 1000 | 1000 | 1000 | 1000 | 1000 | 1000 | 1000 | 1000 | 1000 |
| NaHCO₃ (0.1N) | | 310 prec. | 310 prec. | 310 prec. | 310 prec. | 310 prec. | 310 prec. | 310 prec. | 310 prec. | 310 prec. |
| Glutamic acid (5.9 mg/ml) μl | | 800 | 800 | 800 | 800 | | | | | |
| Aspartic acid (5.3 mg/ml) μl | | | | | | 800 | 800 | | | |
| Tartaric acid (6 mg/ml) μl | | | | | | | | 800 | 400 | 800 |
| Meglumine (60 mg/ml) μl | | | | 100 | 50 | | 50 | | | 50 + 50 |
| Ascorbic acid 5% μl | | | 100 | 100 | | | | | | |
| Water μl | | 200 | 100 | | 150 | 200 | 150 | 200 | 600 | 150 |
| APO/Acid ratio | | 1 to 1 | 1 to 1 | 1 to 1 | 1 to 1 | 1 to 1 | 1 to 1 | 1 to 1 | 1 to 0.5 | 1 to 1 |
| Solutions appearance | trans. | trans. | trans. | trans. | trans. | trans. | trans. | trans. | trans. | trans. |
| pH | | 4.19 | 3.54 | 3.29 | 4.18 | 4.34 | 3.60 | 4.21 | 2.85 | 3.19 | 3.60 |
| Total μl | 1000 | 1000 | 1000 | 1000 | 1000 | 1000 | 1000 | 1000 | 1000 | 1000 | prec. = precipitated;
trans. = transparent

Example 2. Preparation of Apomorphine Salt Solution/Formulation for Subcutaneous Administration Apomorphine-HCl hemi-hydrate was dissolved in 0.1% sodium bisulfite solution to form 1% apomorphine solution. Apomorphine was precipitated by adding the appropriate amount of 0.1 N sodium bicarbonate solution. The precipitate was washed twice with water. The precipitated apomorphine base was dissolved with 1.47% glutamic acid solution to form a final 2.5% apomorphine solution at a 1:1 molar ratio with the glutamic acid. In some instances, ascorbic acid and/or meglumine and/or arginine solutions were added to the apomorphine-glutamate solution to Obtain a final concentration of 0.5%, 0.6% or 0.56%, respectively. Table 2 shows the composition of apomorphine formulations which were prepared as described above.

TABLE 2

Composition of apomorphine formulations

| Formulation No. | 1 | 2 |
|---|---|---|
| APO•HCl (10 mg/ml) µl | 1250 | 1250 |
| NaHCO$_3$ 0.1N | 412 precipitated | 412 precipitated |
| Glutamic acid (14.7 mg/ml) µl | 400 | 400 |
| Meglumine (60 mg/ml) µl | | 50 |
| L-arginine (56 mg/ml) | | |
| Ascorbic acid 5% µl | | 50 |
| Water µl | 100 | |
| APO/Acid ratio | 1 to 1 | 1 to 1 |
| APO conc. (mg/ml) | 25 | 25 |
| Solutions appearance | transparent | transparent |
| pH | 3.60 | 4.13 |
| Total µl | 500 | 500 |

Example 3. Physical Stability of Apomorphine Salt Solutions In Vitro

Various apomorphine salt solutions were examined for stability after sitting at room temperature for a period of time. The results of the study are shown in Table 3. Notably, apomorphine salt solutions containing asparate, glutamate, tartrate, maleate and optionally meglumine were stable over the examined time range.

TABLE 3

Composition of apomorphine salt solutions for stability testing

| API | | Acid | | Anti- | | | |
|---|---|---|---|---|---|---|---|
| Name | Amount | name | Other | oxidant | pH | Color | Precipitation |
| Apomorphine-HCl (Apo-Go ®) | 1% | HCl | Examined after 50 hrs at RT, 8 hrs at 40° C. and 48 hrs at RT | Na-bisulfite | 3.5 | Slightly greenish | Yes |
| Apomorphine | 1% | Ascorbate | | Ascorbic | 4.0 | Greenish | No |
| Apomorphine | 1% | Ascorbate | | Ascorbic | 3.3 | Greenish | No |
| Apomorphine | 1% | Glutamate | | — | 3.5 | Colorless | No |
| Apomorphine | 1% | Aspartate | | — | 3.1 | Colorless | No |
| Apomorphine | 2.5% | Tartarate | Examined after 48 hrs at RT | — | 2.5 | Colorless | No |
| Apomorphine | 2.5% | Maleate | | — | 2.8 | Colorless | No |
| Apomorphine | 2.5% | Citrate | | — | 2.4 | Grayish | No |
| Apomorphine | 2.5% | Succinate | | — | 3.5 | Colorless | Yes |
| Apomorphine | 2.5% | Ascorbate | | Ascorbic | 3.6 | Greenish | No |
| Apomorphine | 2.5% | Ascorbate | Meglumine* | Ascorbic Cysteine | 4.2 | Greenish | No |
| Apomorphine-HCl (Apo-Go ®) | 1% | HCl | * | — | 3.5 | Slightly greenish | No |
| Apomorphine | 1% | Glutamate | * | — | 3.5 | Colorless | No |
| Apomorphine | 1% | Glutamate | * | Ascorbic | 3.2 | Greenish | No |
| Apomorphine | 1% | Glutamate | Meglumine* | Ascorbic | 4.2 | Grayish | No |
| Apomorphine | 1% | Glutamate | Meglumine* | — | 4.3 | Colorless | No |
| Apomorphine | 1% | Aspartate | * | — | 3.6 | Colorless | No |
| Apomorphine | 1% | Aspartate | Meglumine* | — | 4.2 | Colorless | No |
| Apomorphine | 1% | Tartarate | * | — | 2.9 | Colorless | No |
| Apomorphine | 1% | Tartarate | * | — | 3.2 | Colorless | No |
| Apomorphine | 1% | Tartarate | Meglumine* | — | 3.6 | Colorless | No |

* Examined after 48 hrs at room temperature (RT)

Example 4. Preparation of Apomorphine Salt Solution/Formulation for Subcutaneous Administration Apomorphine-HCl hemi-hydrate was dissolved in 0.1% sodium bisulfite solution to form a 1% apomorphine solution. Apomorphine was precipitated by adding the appropriate amount of 0.1 N sodium bicarbonate solution. The precipitate was washed twice with water. The precipitated apomorphine base was dissolved with 0.94% glutamic acid solution to form a final concentration of 1% or 1.5% apomorphine solution at 1:1 molar ratio with the glutamic acid, in some instances, ascorbic acid and/or meglumine and/or arginine solutions were added to the apomorphine-glutamate solution to obtain a final concentration of 0.5%, 0.6%, or 0.56%, respectively. Table 4 shows the composition of apomorphine formulations which were prepared as described above.

TABLE 4

Composition of apomorphine formulations

| Formulation No (%) | 1 | 2 | 3 | 4 | 5 | 6 | 7 | 8 |
|---|---|---|---|---|---|---|---|---|
| APO•HCl (10 mg/ml) μl | 1000 | 1500 | 1000 | 1500 | 1000 | 1500 | 1000 | 1500 |
| NaHCO$_3$ 0.1N | 330 | 495 | 330 | 495 | 330 | 495 | 330 | 495 |
|  | prec. | prec. | prec. | prec. | prec. | prec. | prec. | prec. |
| Glutamic acid (9.4 mg/ml) μl | 500 | 750 | 500 | 750 | 500 | 750 | 550 | 826 |
| Meglumine (60 mg/ml) μl |  |  | 100 | 100 |  |  | 100 | 87 |
| L-Arginine (56 mg/ml) |  |  |  |  | 100 | 100 |  |  |
| Ascorbic acid 5% μl |  |  | 100 | 100 | 100 | 100 | 100 | 87 |
| Water μl | 500 | 250 | 300 | 50 | 300 | 50 | 250 |  |
| APO/Acid ratio | 1 to 1 | 1 to 1 | 1 to 1 | 1 to 1 | 1 to 1 | 1 to 1 | 1 to 1.1 | 1 to 1.1 |
| APO/conc. (mg/ml) | 10 | 15 | 10 | 15 | 10 | 15 | 10 | 15 |
| Solutions appearance | trans. | trans. | trans. | trans. | trans. | trans. | trans. | trans. |
| pH | 3.83 | 3.76 | 4.40 | 4.27 | 4.46 | 4.32 | 4.41 | 4.20 |
| Total μl | 1000 | 1000 | 1000 | 1000 | 1000 | 1000 | 1000 | 1000 | prec. = precipitated;
trans. = transparent

Example 5. Effect of Formulation Composition on Apomorphine-dependent SC Staining Following Continuous Subcutaneous Infusion into Full Thickness Pig Skin, Ex Vivo Various apomorphine-salt formulations were prepared and administered subcutaneously by continuous infusion into full thickness pig skin (cutis and subcutis) at a rate of 0.05 ml/h. FIG. 1 shows the system used for the procedure. During infusion, the apomorphine formulations were incubated at 37° C. for a period of 17 hours.

Figure 2:
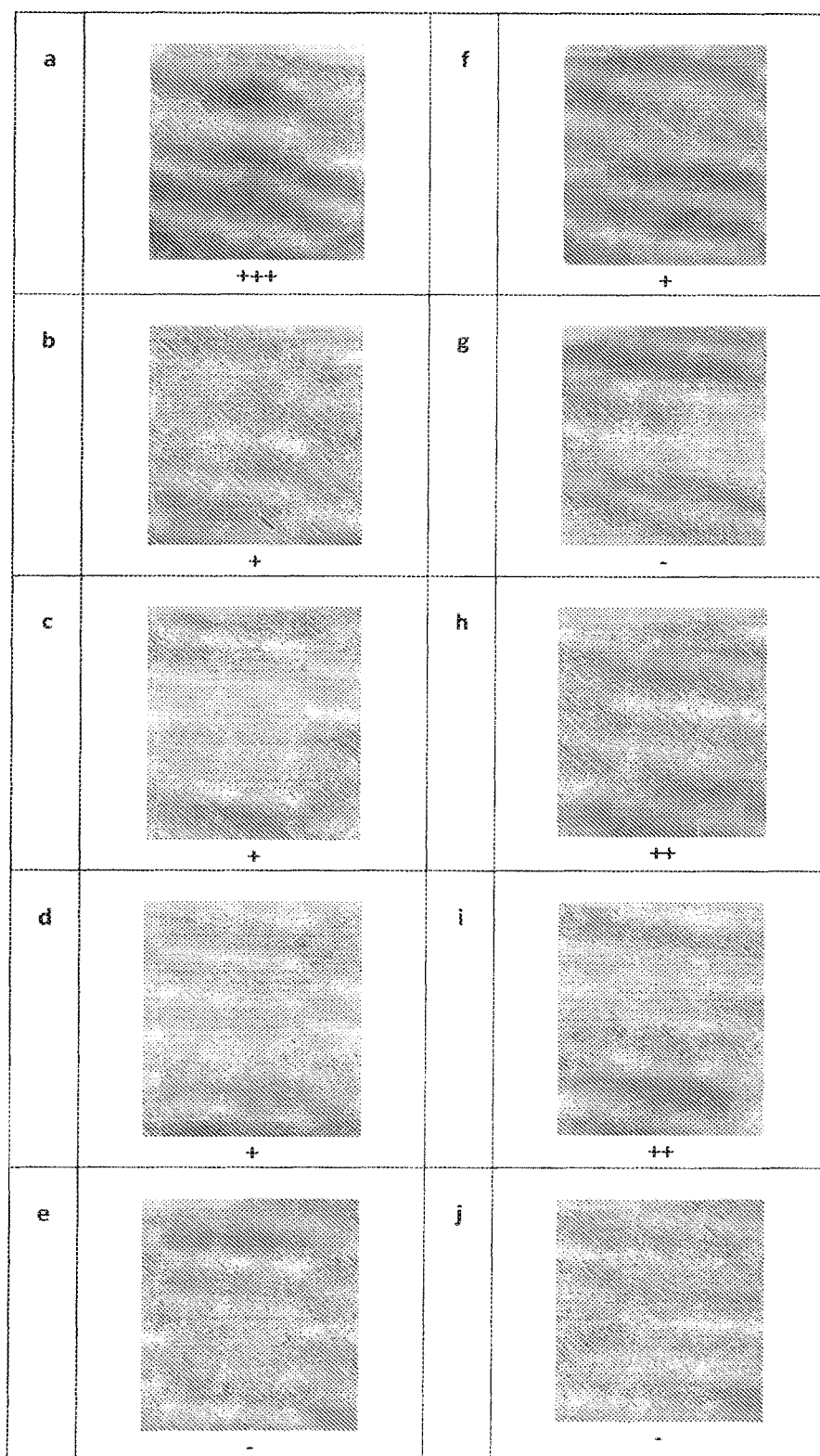
FIG. 2 shows the effect of the formulation composition on apomorphine-dependent skin staining following continuous subcutaneous infusion into full thickness pig skirt of some of the compositions exemplified in Example 3 hereinafter, wherein panel (a) shows 1% apomorphine-HCl (APO- GO®), pH 3.5; panel (b) shows 1% apomorphine-glutamate, 3.5; panel (c) shows 1% apomorphine-glutamate with ascorbic acid, pH 3.3; panel (d) shows 1% apomorphine-glutamate with ascorbic acid and meglumine, pH 4.2; panel (e) shows 1% apomorphine-glutamate with meglumine, pH 4:3: panel (f) shows 1% apomorphine-aspartate, pH 3.6; panel (g) shows 1% apomorphine-aspartate with meglumine pH 4.2: panel (h) shows 1% apomorphine-tartrate, pH 2.9: panel (i) shows 1% apomorphine-semi tartrate, pH 3.2; and panel (j) shows 1% apomorphine-tartrate with meglumine, pH 3.6.

FIG. 2 shows the effect of the formulation composition on apomorphine-dependent skin staining following continuous subcutaneous infusion into full thickness pig skin of some of the compositions listed in Table 3, wherein panel (a) shows 1% apomorphine-HCl (APO-GO®), pH 3.5; panel (b) shows apomorphine-glutamate, pH 3.5; panel (c) shows 1% apomorphine-glutamate with ascorbic acid, pH 3.3; panel (d) shows 1% apomorphine-glutamate with ascorbic acid and meglumine, pH 4.2; panel (e) shows 1% apomorphine-glutamate with meglumine, pH 4.3; panel (f) shows 1% apomorphine-aspartate, pH 3.6; panel (g) shows 1% apomorphine-aspartate with meglurnine pH 4.2; panel (h) shows 1% apomorphine-tartrate, pH 2.9; panel (i) shows 1% apomorphine-hemi tartrate, pH 3.2; and panel (j) shows 1% apomorphine-tartrate with meglumine, pH 3.6. As shown in FIG. 2, the formulation containing 1% apomorphine-HCl (APO-GO®) caused the most severe staining of pig skin ex vivo. Notably, apomorphine salt formulations containing acidic amino acids (aspartate and glutamate) and optionally meglumine caused significantly less staining of pig skin than apomorphine-tartrate and, HCl salts.

Example 6. Preparation of Glutamate, Aspartate and Tartrate Salts of Apomorphine Apomorphine base preparation was performed in the following manner. Apomorphine hydrochloride (Johnson Maltey, Macfarlan Smith) was dissolved in 0.1% Sodium metabisulfite solution (10 mg/ml). Sodium bicarbonate solution at 0.4 M was slowly added to the solution with stirring. The mixture was then stirred for 30 minutes at room temperature. The white precipitate that formed was filtered under nitrogen, washed twice with sterile water and dried in a vacuum oven under dry nitrogen flow for 4 hours. The yield of apomorphine dry base was 75.5%.

Apomorphine salts were prepared by dissolving the apomorphine dry base in the appropriate acid solution at molar ratios ranging between 1:0.5 and 1:1.5.

Apomorphine glutamate solution was prepared by dissolving apomorphine base in 0.1 M glutamic acid solution. Water was added to obtain solutions with a molar ratio of 1:1 or 1:1.2, apomorphine:glutamic acid, at a final concentration of 2% apomorphine. The pH of each solution was 4.7 and 4.4, respectively.

Apomorphine aspartate solution was prepared by dissolving apomorphine base in 0.1 M aspartic acid solution. Water was added to obtain a molar ratio of 1:1, apomorphine:aspartic acid, at a final concentration of 2% apomorphine. The pH of the solution was 4.9.

Apomorphine tartrate solution was prepared by dissolving apomorphine base in 0.1 M tartaric acid solution. Water was added to obtain solutions with a molar ratio of 1:1 or 1:0.5, apomorphine:tartaric acid, at a concentration of 2% apomorphine. The pH of each solution was 3.45 and 4.0, respectively.

Apomorphine malate solution was prepared by dissolving apomorphine base in 0.1 M tartaric acid solution. Water was added to obtain solutions with a molar ratio of 1:1 apomorphine:malic acid, at a concentration of 2% apomorphine. The pH of each solution was 4.0. Table 5 shows the composition of each apomorphine organic salt solution.

Example 7. Preparation of Apomorphine-glutamate Formulations with Tween-80

Apomorphine-glutamate solutions were prepared in the following manner. Antioxidants were dissolved in water to obtain a 1% antioxidants solution. Tween-80 was dissolved in the antioxidants solution to obtain a final concentration of 4% Tween-80. The 4% Tween/antioxidants solution was further diluted in antioxidants solution to obtain the desired final concentration of Tween-80. Apomorphine base and glutamic acid were then weighed to obtain the desired molar ratio (e.g., 1:1 to 1:1.5). The prepared Tween-80/antioxidants solution was added and the solution was stirred until dissolution occurred.

products of apomorphine in the formulated solutions at various time points. Table 9 shows the stability of apomorphine in the apomorphine-hydrochloride and apomorphine-glutamate solutions as measured in milligrams of apomorphine per gram of solution at various time points following exposure to physiological conditions. Table 10 shows the production of degradation products of apomorphine in the solutions at various time points following exposure to physiological conditions. Degradation products in Tables 8 and 10 are shown as a percent of apomorphine peak area as measured by high-performance liquid chromatography (HPLC).

TABLE 5

Composition of organic acid salts of apomorphine

| Formulation No. (%) | 1 | 2 (1:1.2) | 3 (1:1.2) | 4 | 5 | 6 (1 eq) | 7 (1/2 eq) | 8 | 9 | 10 |
|---|---|---|---|---|---|---|---|---|---|---|
| APO-GO (µl) | | | | | | | | | | 2500 |
| APO base (mg) | 50 | 50 | 50 | 25 | 50 | 50 | 50 | 50 | 25 | |
| Glutamic acid 14.7 mg/ml (µl) | 1873 | 2250 | 2250 | 938 | | | | | | |
| Aspartic acid 13.3 mg/ml (µl) | | | | | 1875 | | | | 938 | |
| Tartaric acid 15 mg/ml (µl) | | | | | | 1875 | 938 | | | |
| Malic acid 13.4 mg/ml (µl) | | | | | | | | 1875 | | |
| Meglumine 60 mg/ml (µl) | | | 125 | | | | 188 | | | |
| Water (µl) | 627 | 250 | 125 | 1560 | 625 | 439 | 1562 | 625 | 1560 | |
| Total volume (µl) | 2500 | 2500 | 2500 | 2500 | 2500 | 2500 | 2500 | 2500 | 2500 | |
| APO (mg/ml) expected | 20 | 20 | 20 | 10 | 20 | 20 | 20 | 20 | 10 | 10 |
| pH | 4.68 | 4.40 | 4.76 | 4.69 | 4.93 | 3.45 | 3.98 | 3.98 | 4.59 | 3.90 |

Example 8. Comparison of Stability Between Apomorphine-glutamate Solutions and Commercially Available Apomorphine-HCl Solutions The stability of apomorphine-glutamate formulations containing 1% apomorphine, was compared to APO-G®, a commercially available form of 10 mg/ml (1%) apomorphine-HCl solution. Comparisons were performed under physiological conditions approximated by diluting the solutions at 1:10 with phosphate-buffered saline solution, pH 7.5 (PBS). Table 6 shows the composition of the apomorphine-glutamate solutions referred to as ND1 and ND2—which were synthesized for comparison to commercially available apomorphine-hydrochloride solution. Table 7 shows the stability of apomorphine in the apomorphine-hydrochloride and apomorphine-glutamate solutions as measured in milligrams of apomorphine per gram of solution at various time points following synthesis of the apomorphine-glutamate solutions. Table 8 shows the production of degradation

TABLE 6

Composition of apomorphine-glutamate formulations for stability analysis

| Ingredient (%) | ND1 | ND2 |
|---|---|---|
| Apo base (FW 267.32) | 1.0 | 1.0 |
| Glutamic acid (FW 147.13) | 0.8 | 0.8 |
| Tween-80 | 0.5 | 2.0 |
| Anti-oxidants | 0.6 | 0.6 |

TABLE 7

Apomorphine stability (mg apomorphine/g solution) in spomorphine-glutamate and apomorphine-hydrochloride solutions at different time points

| Sample ID | t = 0 hours | t = 4 hours | t = 6 days |
|---|---|---|---|
| ND1 | 9.9 | 10.0 | 10.0 |
| ND2 | 10.0 | 10.1 | 10.1 |
| Apo-Go ® | 11.8 | ND | ND |

ND = Not determined

TABLE 8

Degradation products of apomorphine produced in formulations as a percent of peak area (% of apomorphine peak area)

| | Unknown r.t.: 5.5 min. | | | Unknown r.t.: 6.9 min. | | |
|---|---|---|---|---|---|---|
| Sample ID | t = 0 hours | t = 24 hours | t = 6 days | t = 0 hours | t = 24 hours | t = 6 days |
| ND1 | 0.12 | 0.12 | 0.11 | 0.08 | 0.08 | 0.10 |
| ND2 | 0.09 | 0.09 | 0.09 | 0.07 | 0.07 | 0.09 |
| Apo-Go ® | 0 | ND | ND | 0.03 | ND | ND |

ND = Not determined

TABLE 9

Apomorphine stability (mg apomorphine/g solution) following exposure to physiological conditions (1:10 dilution in PBS)

| Sample ID | t = 0 hours | t = 24 hours | t = 6 days |
|---|---|---|---|
| ND1 | 0.92 | 0.94 | 0.90 |
| ND2 | 0.95 | 0.94 | 0.92 |
| Apo-Go ® in PBS + 2% Tween-80 | 1.10 | 1.04 | 0.27 |
| Apo-Go ® in PBS + 0.5% Tween-80 | 1.11 | 0.94 | NA |

ND = Not Applicable; Concentration of apomorphine in Apo-Go ® solution 6 days after exposure to physiological conditions is shown in gray.

TABLE 10

Degradation products of apomorphine produced under physiological conditions (1:10 dilution in PBS) as a percent of peak area (% of apomorphine peak area)

| | Unknown r.t.: 5.5 min. | | | Unknown r.t.: 6.9 min. | | | r.t.: 13.1 min. | r.t.: 20.85 min. |
|---|---|---|---|---|---|---|---|---|
| Sample ID | t = 0 hours | t = 24 hours | t = 6 days | t = 0 hours | t = 24 hours | t = 6 days | t = 6 days | t = 6 days |
| ND1 | 0.14 | 0.15 | 0.14 | 0.08 | 0 | 0.12 | 0 | 0 |
| ND2 | 0.09 | 0.10 | 0.09 | 0.07 | 0 | 0 | 0 | 0 |
| Apo-Go ® in PBS + 2% Tween-80 | 0.26 | 5.23 | 36.3 | 0.10 | 1.41 | 4.47 | 1.02 | 5.5 |
| Apo-Go ® in PBS + 0.5% Tween-80 | 0.23 | 12.77 | NA | 0.16 | 2.55 | NA | NA | NA |

NA = Not Applicable; Concentration of apomorphine in Apo-Go ® solution 1 and 6 days after exposure to physiological conditions are shown in gray.

The results clearly demonstrated that under physiological conditions the glutamic acid salt of apomorphine was stable for at least 6 days at room temperature, whereas the commercial product APO-GO® was extensively degraded. Tween-80 at a concentration of 0.5% was sufficient to maintain chemical stability of apomorphine-glutamate solution, while even 2% Tween-80 was not sufficient to maintain chemical stability of Apomorphine-110 (APO-GO®) solution.

Example 9. Analysis of Formulation Components on Apomorphine-glutamate Solution Stability The effect of Tween-80, antioxidants, and the molar ratio of acid to apomorphine on the physical stability of apomorphine-glutamate salt formulations under physiological conditions was tested by diluting the formulations at 1:10 or 1:20 with PBS. The composition of each of the tested formulations (F1-5) is shown in Table 11. Each component is shown as a percent of the total solution.

TABLE 11

Apomorphine glutamate salt formulations

| Ingredient (%) | F1 | F2 | F3 | F4 | F5 |
|---|---|---|---|---|---|
| Apomorphine | 2.0 | 2.0 | 2.0 | 2.0 | 2.0 |
| Glutamic acid | 1.3 | 1.3 | 1.6 | 1.6 | 1.6 |
| Tween-80 | 2.0 | 2.0 | 0 | 2.0 | 5.0 |
| Antioxidants | 0 | 0.6 | 0.6 | 0.6 | 0.6 |
| Apo:Glut (molar ratio) | 1:1.18 | | | 1:1.45 | |

Samples of each formulation were diluted in freshly prepared PBS as shown in Tables 12 and 13. Samples of formulations F1-F3 were diluted in PBS at 1:20 (Table 11). Samples of formulations F4 and F5 were diluted in PBS at 1:10 and 1:20. The appearance of each solution was observed 20 minutes and 5 hours after dilution, and pH and Tween concentration were measured.

TABLE 12

Observations of formulations F1, F2 and F3 following 1:20 dilution

| | Dilution 1:20 | | |
|---|---|---|---|
| | F1 | F2 | F3 |
| 20 minutes | Micellar | Transparent | Precipitated |
| 5 hours | Blue/Precipitated | Precipitated | Precipitated |
| pH measured | 7.45 | 7.34 | 7.31 |
| Tween-80 concentration after dilution | 0.1 | 0.1 | 0 |

TABLE 13

Observations of formulations F4 and F5 following 1:10 or 1:20 dilution

|  | Dilution 1:10 | | Dilution 1:20 | |
| --- | --- | --- | --- | --- |
|  | F4 | F5 | F4 | F5 |
| 2 hours | Micellar | Micellar | Transparent | Transparent |
| 5 hours | Micellar | Micellar | Micellar | Micellar |
| pH measured | 7.09 | 7.07 | 7.34 | 7.32 |
| Tween-80 concentration after dilution | 0.1 | 0.25 | 0.1 | 0.25 |

Following dilution of the formulations with PBS, the formulations were physically stable for at least 5 hours only if they contained Tween-80, antioxidants, and glutamic acid at a molar ratio of greater than 1:1.2, apomorphine:glutamic acid. In the absence of Tween-80 and at a molar ratio of 1:1.18, apomorphine:glutamic acid, the formulations were not physically stable at a pH of 7 to 7.5 (see Tables 11 and 12, formulation F3). In the absence of antioxidants, the solution turned blue (see Tables 11 and 12, formulation F1).

Figure 3:
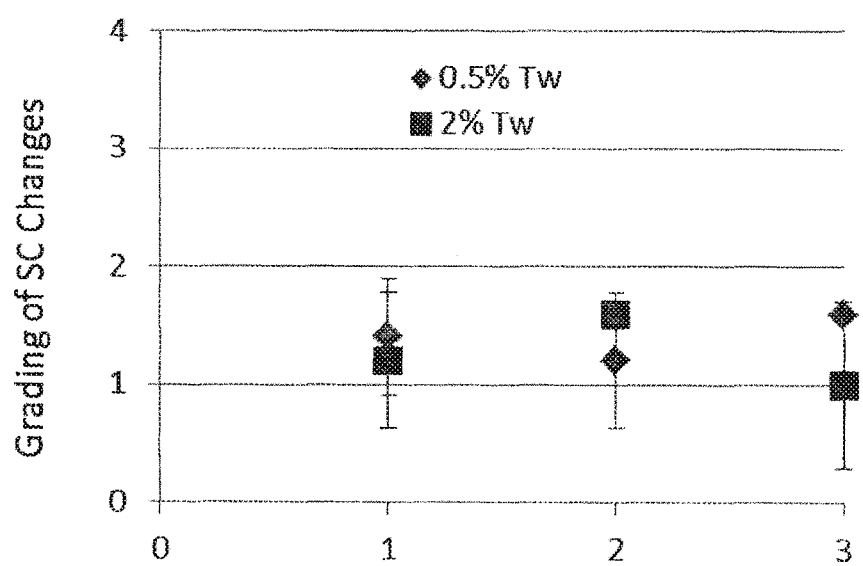
FIG. 3 shows histological grading of skin samples (Grading of Subcutis (SC) Changes) 1, 2 or 3 weeks after subcutaneous administration of apomorphine solution containing 0.5% or 2.0% Tween-80.

Example 10. Analysis of Skin Inflammation Following Subcutaneous Administration of Apomorphine Formulations Formulations containing 1% apomorphine and glutamic acid at a molar ratio of 1:1.5, were continuously administered subcutaneously to pigs, at a rate of 4 ml/24 h via a mini-pump. Commercially available 1% apomorphine-HCl (Apo-Go®) was also administered separately to allow for comparison of effects generated by administration of each agent. The formulation of each solution administered is shown in Table 14. Skin samples were collected 1, 2, or 3 weeks post-infusion and subjected to histopathological evaluation. Results are shown in Table 15. The sites that were infused with the apomorphine-glutamate formulations were characterized by minimal to mild chronic subcutaneous inflammation, whereas the commercial apomorphine-HCl preparation exhibited severe subcutaneous inflammation with necrosis (see the gray boxes in Table 15). There was no difference in the severity of lesions observed between the sites administered with formulations containing 0.5% or 2% Tween-80 as shown in FIG. 3.

TABLE 14

Formulations for Subcutaneous Administration

|  |  | Formulation | | |
| --- | --- | --- | --- | --- |
|  |  | 1 | 2 | Apo-Go ® |
| Ingredient (%) | Apo base | 1.00 | 1.00 | — |
|  | Apo-HCl | — | — | 1.00 |
|  | Glutamic acid | 0.82 | 0.82 | — |
|  | Tween-80 | 0.50 | 2.00 | — |
|  | Antioxidants | 0.6 | 0.6 | 0.1 |

TABLE 15

Histological evaluation of skin exposed to apomorphine formulations

|  | Sample collection | | | | | | |
| --- | --- | --- | --- | --- | --- | --- | --- |
|  | 3 weeks post-application | | 2 weeks post-application | | 1 week post-application | | |
|  | Formulation | | | | | | |
|  | 1 | 2 | 1 | 2 | 1 | 2 | ApoGo ® |
|  | | | | Subcutis | | | |
| Chronic Inflammation | 2 | 1 | 1.5 | 2 | 1.75 | 1.5 | 4 |
| Cavity with Amorphous Eosinophilic Material | 0 | 0 | 0 | 0 | 0.25 | 0.25 | 0 |
| Necrosis | 0 | 0 | 0 | 0 | 0 | 0 | 2 |

Grading of histological changes: 0 = No change, 1 = Minimal change, 2 = Mild change, 3 = Moderate change, 4 = Marked change As shown in Tables 16, 17 and 18, HPLC analysis demonstrated that the stability of the tested formulations containing 0.5% or 2% Tween-80 (identified as ND1 and ND2) was similar between 4 and 6 days after preparation. The average apomorphine concentrations (AVG mg/g) are shown in in Tables 16 and 17.

TABLE 16

Analysis of apomorphine solutions 4 days post-formulation preparation

| Sample ID | Sample | Weight (mg) | HPLC (ppm) | Dilution | Apomorphine (mg/g) | AVG (mg/g) | STDEV | RSD (%) |
| --- | --- | --- | --- | --- | --- | --- | --- | --- |
| ND1 | ts1 | 104.80 | 106.827 | 10 | 10.193 | 10.17 | 0.04 | 0.4 |
|  | ts2 | 103.60 | 105.046 | 10 | 10.140 |  |  |  |
| ND1a | ts1 | 102.90 | 103.895 | 10 | 10.097 | 10.10 | NA | NA |
| ND2 | ts1 | 100.01 | 99.409 | 10 | 9.940 | 9.97 | 0.04 | 0.4 |
|  | ts2 | 97.85 | 97.852 | 10 | 10.000 |  |  |  |

TABLE 17

Analysis of apomorphine solutions 5 days post-formulation preparation

| Sample ID | Sample | Weight (mg) | HPLC (ppm) | Dilution | Apomorphine (mg/g) | AVG (mg/g) | STDEV | RSD (%) |
|---|---|---|---|---|---|---|---|---|
| ND1a | ts1 | 96.85 | 96.968 | 10 | 10.012 | 10.00 | 0.020 | 0.20 |
|  | ts2 | 100.46 | 100.305 | 10 | 9.985 |  |  |  |
| ND2 | ts1 | 98.79 | 100.305 | 10 | 10.153 | 10.09 | 0.086 | 0.85 |
|  | ts2 | 97.40 | 97.708 | 10 | 10.032 |  |  |  |

TABLE 18

HPLC analysis of apomorphine solutions at 0 and 6 days post-formulation preparation

|  | Unknown r.t.: 5.5 min | | Unknown r.t.: 6.9 min | |
|---|---|---|---|---|
| Sample ID | t = 0 | t = 6 days | t = 0 | t = 6 days |
| ND1 | 0.08 | ND | 0.08 | ND |
| ND1a | 0.09 | 0.095 | 0.08 | 0.105 |
| ND2 | 0.09 | 0.095 | 0.075 | 0.105 |

ND—Not Determined

Example 11. Effect of Tween-80 on Apomorphine Solution Stability

The effect of Tween-80 on the physical stability of apomorphine-HCl formulations and apomorphine-glutamate formulations was analyzed. All tested formulations contained proprietary combinations of antioxidants. Observations regarding the color of undiluted solutions and evidence of precipitation in those solutions were recorded after either 4 days or 1 week at 25° C. Additionally, observations regarding evidence of precipitation in diluted solutions were recorded after 4 days at 25° C. A 1:20 dilution of each solution was achieved by placing 2.85 ml of 50 nM PBS at pH 7.5 in a vial and adding 150 µl of each undiluted solution dropwise. The effect of Tween-80 on the stability of undiluted apomorphine-HCl formulations is shown in Table 19. The effect of Tween-80 on the stability of apomorphine-HCl formulations diluted 1:20 in PBS is shown in Table 20. The effect of Tween-80 on stability of apomorphine-glutamate formulations is shown in Table 21. The effect of Tween-80 on the stability of apomorphine-glutamate formulations diluted 1:20 in PBS is shown in Table 22.

TABLE 19

Effect of Tween-80 on stability of undiluted apomorphine-HCl formulations

|  | 1% Apomorphine-HCl, increasing Tween-80 from 0% to 0.5% | | | 2.5% Apomorphine-HCl, increasing Tween-80 from 2% to 4% | | |
|---|---|---|---|---|---|---|
| Ingredient | F-1 | F-2 | F-3 | F-4 | F-5 | F-6 |
| Tween-80 (%) | 0 | 0.25 | 0.50 | 2.00 | 3.00 | 4.00 |
| Stability after 4 days at 25° C. | No color No precipitation | No color No precipitation | No color Precipitated | No color Precipitated | No color No precipitation | No color No precipitation |
| Stability after 1 week at 25° C. | No color Very slight precipitation | No color Precipitated | No color Precipitated | No color Precipitated | No color Slight precipitation | No color Very slight precipitation |

TABLE 20

Effect of Tween-80 on stability of diluted apomorphine-HCl formulations

|  | 1% Apomorphine-HCl, Increasing Tween-80 from 0% to 0.5% | | | 2.5% Apomorphine-HCl, Increasing Tween-80 from 2% to 4% | | |
|---|---|---|---|---|---|---|
| Ingredient | F-1 | F-2 | F-3 | F-4 | F-5 | F-6 |
| Tween-80 (%) | 0 | 0.25 | 0.50 | 2.00 | 3.00 | 4.00 |
| Appearance after 4 days at 25° C. | Slight precipitation | Micellar | Micellar | Not Micellar Very turbid | Not Micellar Very turbid | Not Micellar Very turbid |

TABLE 21

Effect of Tween-80 on stability of undiluted apomorphine-glutamate formulations

| | 1% Apomorphine-Glutamate, Increasing Tween-80 from 0% to 0.5% | | | 2.5% Apomorphine-Glutamate, Increasing Tween-80 from 0% to 4% | | | |
|---|---|---|---|---|---|---|---|
| Ingredient | F-7 | F-8 | F-9 | F-10 | F-11 | F-12 | F-13 |
| Tween-80 (%) | 0 | 0.25 | 0.50 | 0 | 2.00 | 3.00 | 4.00 |
| Stability after 4 days at 25° C. | No color No precipitation | No color No precipitation | No color No precipitation | Very slightly yellow No precipitation | Very slightly yellow No precipitation | Very slightly yellow No precipitation | Very slightly yellow No precipitation |
| Stability after 1 week at 25° C. | No color No precipitation | No color No precipitation | No color No precipitation | No color No precipitation | No color No precipitation | No color No precipitation | No color No precipitation |

TABLE 22

Effect of Tween-80 on stability of diluted apomorphine-glutamate formulations

| | 1% Apomorphine-Glutamate, Increasing Tween-80 from 0% to 0.5% | | | 2.5% Apomorphine-Glutamate, Increasing Tween-80 from 0% to 4% | | | |
|---|---|---|---|---|---|---|---|
| Ingredient | F-7 | F-8 | F-9 | F-10 | F-11 | F-12 | F-13 |
| Tween-80 (%) | 0 | 0.25 | 0.50 | 0 | 2.00 | 3.00 | 4.00 |
| Appearance after 4 days at 25° C. | Precipitated | Almost transparent | Micellar | Strongly precipitated | Micellar Turbid | Micellar Turbid | Micellar |

Precipitation occurred within 1 week at room temperature in all of the tested apomorphine-HCl formulations, whereas no precipitation occurred in any of the tested apomorphine-glutamate formulations. However, following dilution at 1:20 with PBS, both apomorphine salts precipitated in the absence of Tween (e.g., see formulations F-1, F-7, and F-10 in Tables 20 and 22). The 2.5% apomorphine-HCl solution could not be prepared without Tween as it did not dissolve.

Example 12. Comparison of Apomorphine-glutamate and Apomorphine-HCl Formulation Stability UV-HPLC was used to analyze and compare the chemical stabilities of the apomorphine-glutmate and apomorphine-HCl formulations. Table 23 summarizes apomorphine recovery after 1 month at 25° C. from apomorphine salt formulations that include varying amounts of Tween-80. The results documented in Table 23 show that the apomorphine-HCl formulation is less stable than the apomorphine-glutamate formulations of the instant invention.

TABLE 23

Apomorphine recovery from solution after 1 month at 25° C.

| Apomorphine Salt | Tween-80 (%) | Apomorphine recovery (%) |
|---|---|---|
| 1% Apomorphine + Glutamic acid | 0 | 99.0 |
| 1% Apomorphine + Glutamic acid | 0.50 | 101.7 |
| 2.5% Apomorphine + Glutamic acid | 0 | 94.6 |
| 2.5% Apomorphine + Glutamic acid | 2.00 | 98.0 |
| 2.5% Apomorphine + Glutamic acid | 3.00 | 98.3 |
| 2.5% Apomorphine + Glutamic acid | 4.00 | 95.0 |

TABLE 23-continued

Apomorphine recovery from solution after 1 month at 25° C.

| Apomorphine Salt | Tween-80 (%) | Apomorphine recovery (%) |
|---|---|---|
| 1% Apomorphine-HCl | 0 | 89.3 |
| 1% Apomorphine-HCl | 0 | 89.5 |

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that may vary depending upon the desired properties sought to be obtained by the present invention.

INCORPORATION BY REFERENCE

The entire contents of all patent publications, websites, and other references cited herein are hereby expressly incorporated herein in their entireties by reference.

The invention claimed is:

1. A liquid or semi-solid pharmaceutical composition comprising apomorphine, an acidic amino acid, and a pharmaceutically acceptable carrier, wherein the molar ratio of apomorphine to the acidic amino acid is about 1:2.5 to about 1:0.5.

2. The pharmaceutical composition of claim 1, wherein the molar ratio of apomorphine to the acidic amino acid is about 1:1 to about 1:1.5.

3. The pharmaceutical composition of claim 1, wherein the acidic amino acid is glutamic acid.

4. The pharmaceutical composition of claim 1, wherein the composition has a pH greater than about 3.

5. The pharmaceutical composition of claim 4, wherein the composition has a pH between about 3.0 and about 5.5, between about 3.5 and about 5.0, between about 3.5 and about 4.5, between about 4.0 and about 5.0, or between about 4.0 and about 7.5, at 25° C.

6. The pharmaceutical composition of claim 1, comprising at least about 1%, or about 1% to about 4%, by weight apomorphine.

7. The pharmaceutical composition of claim 1, wherein the composition has substantially no precipitation of solids, for at least 48 hours at 25° C.

8. The pharmaceutical composition of claim 1, further comprising a surfactant.

9. The pharmaceutical composition of claim 8, wherein the surfactant is Tween-80.

10. The pharmaceutical composition of claim 1, further comprising a local anesthetic and/or an anti-inflammatory agent.

11. The pharmaceutical composition of claim 10, wherein the local anesthetic is an amide based local anesthetic selected from the group consisting of lidocaine, prilocaine, bupivicaine, levobupivacaine, ropivacaine, mepivacaine, dibucaine, and etidocine, or an ester based local anesthetic selected from the group consisting of procaine, amethocaine, cocaine, benzocaine, and tetracaine, and the anti-inflammatory agent is a non-steroidal anti-inflammatory agent selected from the group consisting of diclofenac, ketorolac, salicylates, ibuprofen, piroxicam, and benzydamine, or a steroidal anti-inflammatory agent selected from the group consisting of prednisone, dexmethasone, betamethasone, hydrocortisone and a salt thereof.

12. The pharmaceutical composition of claim 1, wherein said composition is suitable for subcutaneous, intravenous, intranasal, transdermal, sublingual, intramuscular, buccal, ocular, or intratracheal administration.

13. A method of treating a neurological or movement disease or disorder, or a condition associated therewith, in a patient in need thereof, comprising administering to said patient the liquid or semi-solid pharmaceutical composition of claim 1.

14. The method of claim 13, wherein said neurological or movement disease or disorder is selected from the group consisting of Parkinson's disease, Alzheimer's disease, and akinesia.

15. The method of claim 14, wherein the neurological or movement disease or disorder is Parkinson's disease.

16. The pharmaceutical composition of claim 1, wherein the acidic amino acid is aspartic acid or a combination of glutamic acid and aspartic acid.

* * * * *